US006367478B1

(12) United States Patent
Riggs

(10) Patent No.: US 6,367,478 B1
(45) Date of Patent: Apr. 9, 2002

(54) GAIT BELT COVER

(76) Inventor: Gregory S. Riggs, 2003 Auburn Dr., Louisville, KY (US) 40216

(*) Notice: Subject to any disclaimer, the term of this patent is extended or adjusted under 35 U.S.C. 154(b) by 0 days.

(21) Appl. No.: 09/410,957

(22) Filed: Oct. 5, 1999

(51) Int. Cl.[7] .................................................. A61F 13/00
(52) U.S. Cl. ............................ 128/846; 128/876; 2/338
(58) Field of Search ......................... 602/19; 2/11, 338; 128/846, 876

(56) References Cited

U.S. PATENT DOCUMENTS 738,250 A * 9/1903 Stanley
1,666,099 A * 4/1928 Kingman
1,751,595 A * 3/1930 Nachman
2,065,936 A * 12/1936 Hardie
3,038,558 A * 6/1962 Plummer
4,177,807 A * 12/1979 Ocel et al.
5,127,265 A * 7/1992 Williamson et al.
5,328,733 A * 7/1994 Oxley
5,399,943 A * 3/1995 Benik et al.
5,479,943 A * 1/1996 Kuhnell, III
5,577,515 A * 11/1996 Stout et al.
5,592,946 A * 1/1997 Eddy
5,850,706 A * 12/1998 Evans
5,891,066 A * 4/1999 Borschneck et al.
5,907,877 A * 6/1999 Allgood

* cited by examiner

*Primary Examiner*—Michael A. Brown
*Assistant Examiner*—Lalita M Hamilton
(74) *Attorney, Agent, or Firm*—John F. Salazar; Middleton Reutlinger

(57) ABSTRACT

A shirrable cover for a gait belt or other similar belt includes a sleeve, a flap and restraining means whereby the cover may be drawn into a shirred bundle. Such belt cover may consist of various materials and fabric finishes. One embodiment of the shirrable cover includes a back panel and front panel and a flap unitary with the back panel and extending beyond a terminating end of the front panel. Preferably, at least one thread extends along a top seam of the junction of the front and back panels and extends beyond the top seam at least one point. Also, at least one thread extends along the bottom seam of the junction of the front and back panels and extends beyond the bottom seam at least one point.

2 Claims, 4 Drawing Sheets

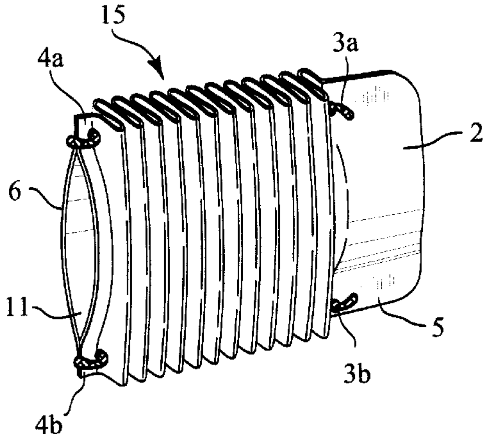
FIG. 7
FIG. 8
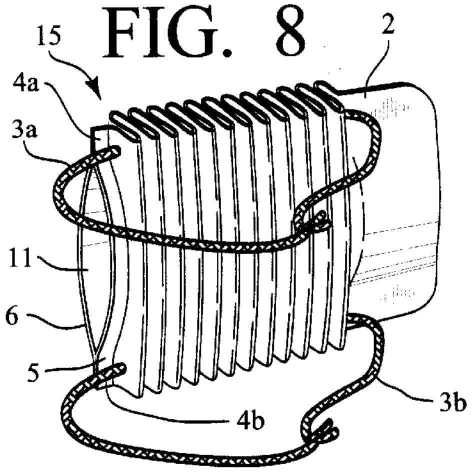
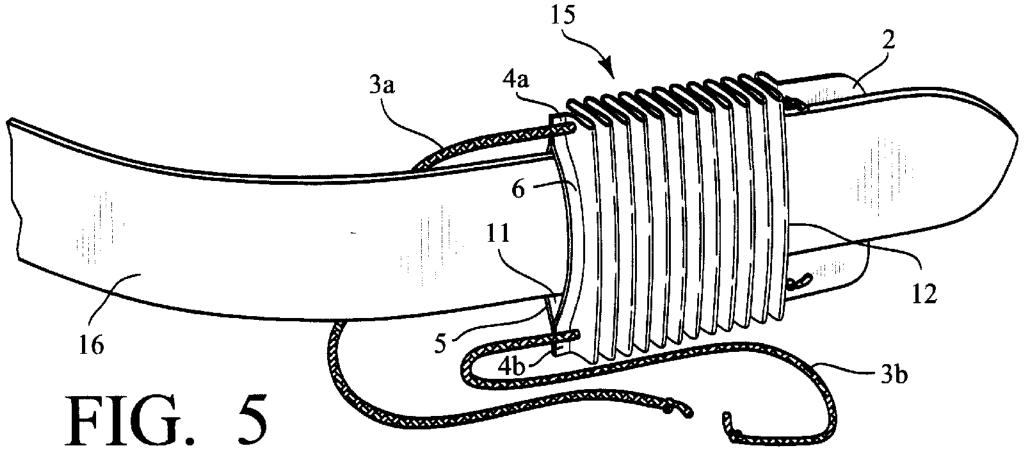
FIG. 5
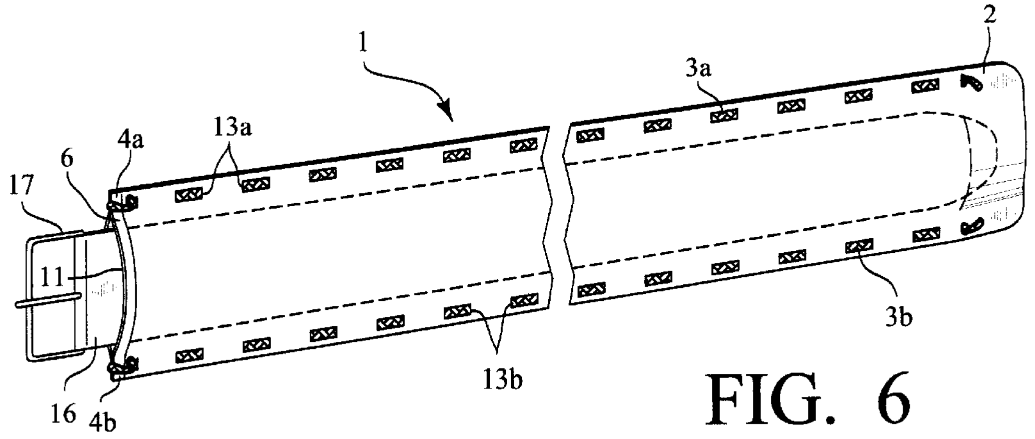
FIG. 6

FIG. 9
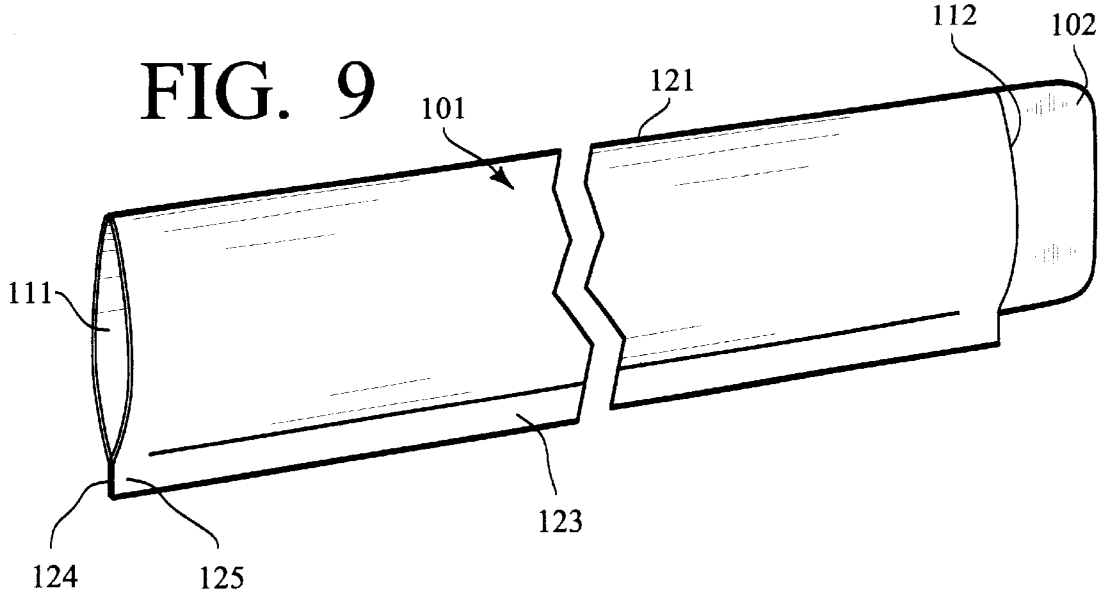
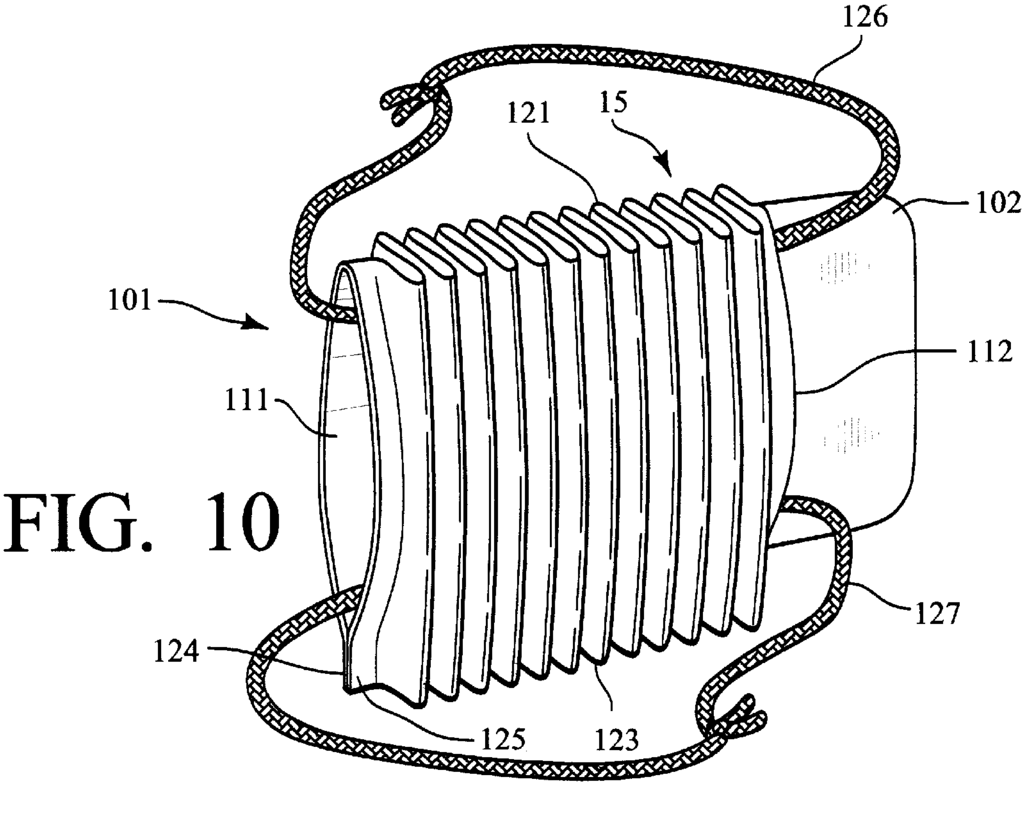
FIG. 10

GAIT BELT COVER

BACKGROUND OF THE INVENTION

1. Field of the Invention

The invention relates generally to gait belts that are used in the medical field for supporting and moving patients. More particularly, the present invention relates to a shirrable protective cover that may be applied to a gait belt.

2. Discussion of the Prior Art

Generally, in medical settings, gait belts are used repeatedly on large numbers of patients. The universal precautions promulgated by the Occupational Safety and Health Administration direct the use of barriers to prevent pathogen transmission between individuals. The repeated use of an uncovered gait belt in transporting patients can provide a route for pathogen transmission between patients. It, therefore, is necessary to use a gait belt cover that prevents direct contact between the belt and the patient.

Repeated use of a gait belt during the course of a day on multiple patients necessitates use of a belt cover that is both effective at preventing pathogen transmission and simple to use. Currently, gait belts are sometimes laundered between uses, instead of covered during use. This method for preventing pathogen transmission is time consuming and unreliable, unless performed diligently. Thus, a need exists for an effective, efficient alternative.

Furthermore, an effective, efficient belt cover would be useful in other settings where hygiene matters. Such a belt cover would facilitate good hygiene practice in industrial situations where back support belts are shared by personnel or where contamination of a belt, due to environmental conditions, is probable. Also, such a belt cover would benefit fitness facilities and other entities that lend support belts to their patrons. All of these situations potentially provide pathogen transmission routes via belt use. Such a belt cover would provide a simple to use barrier to such potential transmission.

SUMMARY OF THE INVENTION

It is an object of the present invention to provide a gait belt cover that is both effective in preventing pathogen transmission and easy to use.

It is another object of the present invention to provide a gait belt cover that can be shirred during or after production, maintained in a shirred state, and then applied to a gait belt in a shirred state, thereby facilitating its application to the belt.

It is another object of the present invention to provide a gait belt cover that forms a barrier around the entire belt, including the buckle.

It is another object of the present invention to provide a shirrable belt cover that may be used in a variety of settings where possible pathogen transmission can occur due to the conditions under which safety belts are worn.

It is a further object of the present invention to provide a shirrable belt cover that does not require any sort of applicator device to apply the cover to a belt.

It is a further object of the present invention to provide a shirrable belt cover that is disposable after one use.

More particularly, the present invention provides a gait belt cover including: a front panel having upper and lower edges, a back panel having upper and lower edges of equal dimensions as those edges on the front panel, and a flap extending longitudinally beyond the upper and lower edges of the back panel. The front and back panels may be rectangular or similar in shape so as to accommodate a belt. A top seam and a bottom seam are formed in a cover by joining the top edges of the front and back panels and the bottom edges of the panels. One or more threads are housed longitudinally within the top and bottom seams, and extend beyond these seams, so that the thread may be drawn out of the seam, thereby shirring the cover. A sleeve is formed by the joining of the panel members at said top seam and said bottom seam with openings at both ends wherein a belt may be inserted.

Preferably, the front and back panels and threads are composed of a shirrable, flexible, substantially impervious material such as a shirrable plastic or synthetic fiber, for example polyethylene, polypropylene, polyvinyl chloride, cotton, rayon or other similar plastic or synthetic or natural fiber, or combinations thereof. Those materials of construction selected maybe chosen from among materials that have been chemically treated to impart a fire retardant finish. Such finishes may consist of organic halides or similar compounds that are introduced into the fabric prior to the fabrication of the cover. The front and back panels may be cut from one of the materials listed above that may or may not have been chemically treated in the aforementioned manner. The panels may be secured one to another by heat sealing, sewing or another appropriate method known in the art that provides a substantially impervious seam where the panels are joined and thereby forming a sleeve. The threads that are housed within the seams may be inserted during heat treatment or sewing, or after these steps.

In one embodiment of the present invention, the thread or threads may be tied off after shirring to maintain the cover in a shirred state. The threads may then be broken to unshirr the cover when needed. In this embodiment, the threads would be of a gauge that could easily be broken by the user during application.

In another embodiment, the thread or threads can be used to shirr the cover and then wrapped around it to maintain it in a bundle. During application of the cover, the user could then unwrap the threads from around the cover to unshirr it. In this embodiment, the thread gauge could be greater than that used in the embodiment listed above, where the thread is broken prior to unshirring the cover.

In another embodiment, the belt cover may comprise one panel that is folded once and has one seam formed by the joining of two edges of the panel. Once the belt is shirred, it may be maintained in a bundle by looping at least two threads, bands, clips, other similar restraining devices or combinations thereof, through the two side openings and around the cover sleeve. These restraining devices may then be knotted, tied or otherwise secured so as to maintain the cover in a shirred state. One of these restraining devices may be disposed within the seam during manufacture, in the same manner as for the embodiment having two seams. The panel may be made from the same materials previously listed.

The belt cover may be shirred into a bundle during or after production and maintained in that state. The restraining device by which the belt cover is maintained in the shirred bundle may be one or more threads, clips, plastic ties, or similar fasteners, or combinations thereof. The bundled cover may then be easily stored or transported for use when and where needed. A gait belt may be inserted into the shirred cover, which may then be unshirred and extended over the gait belt. The cover will thereby form a complete barrier between the gait belt and the wearer. The gait belt in combination with the cover may then be used to support a person without concern for cross-contamination of the belt or the person. After use, the cover can be discarded.

The belt cover may also be used in conjunction with support belts that are designed to support the lower back and abdominal region of the wearer. Such a belt may be inserted into the cover, which is then unshirred so as to cover all of the belt. In this manner, the cover may form a complete barrier between the belt and the wearer.

It is to be understood that the descriptions of the examples of the present invention are not by way of limitation. Various modifications within the scope of the present invention will be apparent to those skilled in the art upon reading the disclosure set forth hereinafter.

BRIEF DESCRIPTION OF THE DRAWINGS

FIG. 5 is a perspective view of the gait belt cover of FIG. 1 showing the shirred cover with a gait belt inserted therein;

FIG. 6 is another perspective view of the combination of the cover and gait belt, showing the cover unshirred and extended thereby enveloping the gait belt;

FIG. 7 is another perspective view of the gait belt cover of FIG. 1 showing the shirred cover with threads 3*a* and 3*b* knotted at the ends;

FIG. 8 is another perspective view of the gait belt cover of FIG. 1 showing the shirred cover with threads 3*a* and 3*b* tied around the outside of the cover;

FIG. 9 is a perspective view of another embodiment of the present invention;

FIG. 10 is a perspective view of the cover of FIG. 9 in a shirred state.

DESCRIPTION OF THE PREFERRED EMBODIMENT

As shown in the figures, a preferred cover of the present invention is designed for use in conjunction with gait belts used to assist in the transporting or support of patients. A gait belt 16, or other type belt may be inserted through the openings 11 and 12 of the cover and, as shown in FIG. 6, the cover 1 may then be unshirred and extended along the belt 16, so as to form a complete barrier between the belt 16 and the wearer, not shown.

Figure 1:
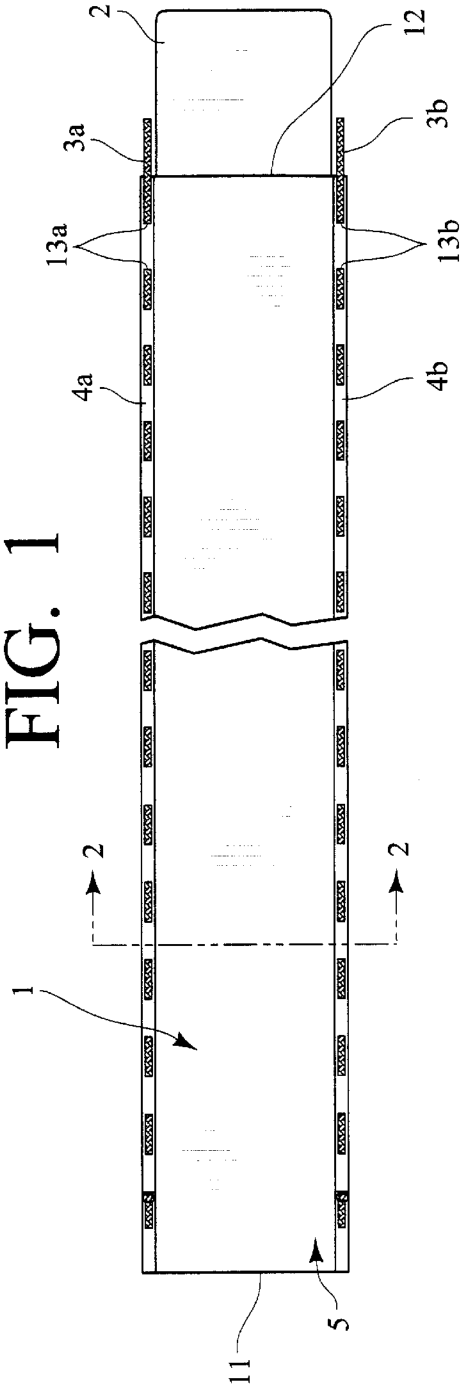
FIG. 1 is a side view of the shirrable gait belt cover of the present invention.

The belt cover 1, shown in FIG. 1, is generally made of a shirrable material, such as, for example, polyethylene, polypropylene, polyvinyl chloride, cotton, rayon or other plastic or fiber, or a combination thereof. Such materials may be chemically or otherwise treated to make them generally fire retardant and/or impervious. The cover 1 comprises a front panel 5 and a back panel 6. The front panel 5 is generally rectangular and is dimensioned to be of similar length and slightly greater width than a belt 17 with which the cover 1 is to be employed. The front panel 5 includes a top edge 7 and a bottom edge 9 that each extends the length of the panel 5.

Figure 2:
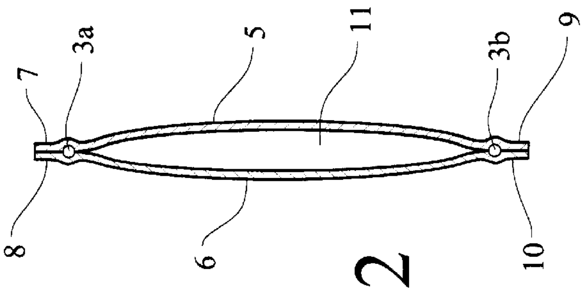
FIG. 2 is a sectional view of FIG. 1 taken along lines 2—2.

The back panel 6 is generally rectangular or similar shape and also includes a top edge 8 and a bottom edge 10. Said top edge 8 and said bottom edge 10 on said back panel 6 are of equal dimensions as said top edge 7 and said bottom edge 9 of said front panel 5, as shown in FIG. 2. The back panel 6 also includes a generally rectangular flap 2 that extends longitudinally along one side of said back panel 6 beyond the ends of said top edge 8 and said bottom edge 10, as shown in FIG. 1.

The preferred dimensions of the cover 1 are approximately 4.5 inches in width and 50 inches in length, with the flap being approximately 4.5 inches in length by 4.5 inches in width, although other dimensions are contemplated within the scope of the invention.

As shown in FIG. 2, the cover 1 is formed by the joining of the top edge 7 of the front panel 5 with the top edge 8 of the back panel 6 and the bottom edge 9 of the front panel 5 with the bottom edge 10 of the back panel 6. The joining of the edges may be accomplished by the application of heat to melt the two edges together, by sewing the panels together or by other similar means. The joined top edge 7 and top edge 8 form top seam 4*a*. The joined bottom edge 10 and bottom edge 9 form bottom seam 4*b*.

The formation of top seam 4*a* and bottom seam 4*b* thereby form opening 11 and opening 12 on either side of front panel 5. The flap 2 on bottom panel 6 extends longitudinally beyond opening 12.

Within top seam 4*a* is one or more top thread 3*a*. Top thread 3*a* extends the length of top seam 4*a*. Top thread 3*a* is partially removable from top seam 4*a* at one or more points 13*a*, as shown in FIG. 3 and FIG. 4.

Within bottom seam 4*b* is one or more bottom thread 3*b*. Bottom thread 3*b* extends the length of bottom seam 4*b*. Bottom thread 3*b* is partially removable from bottom seam 4*b* at one or more points 13*b*.

Figure 3:
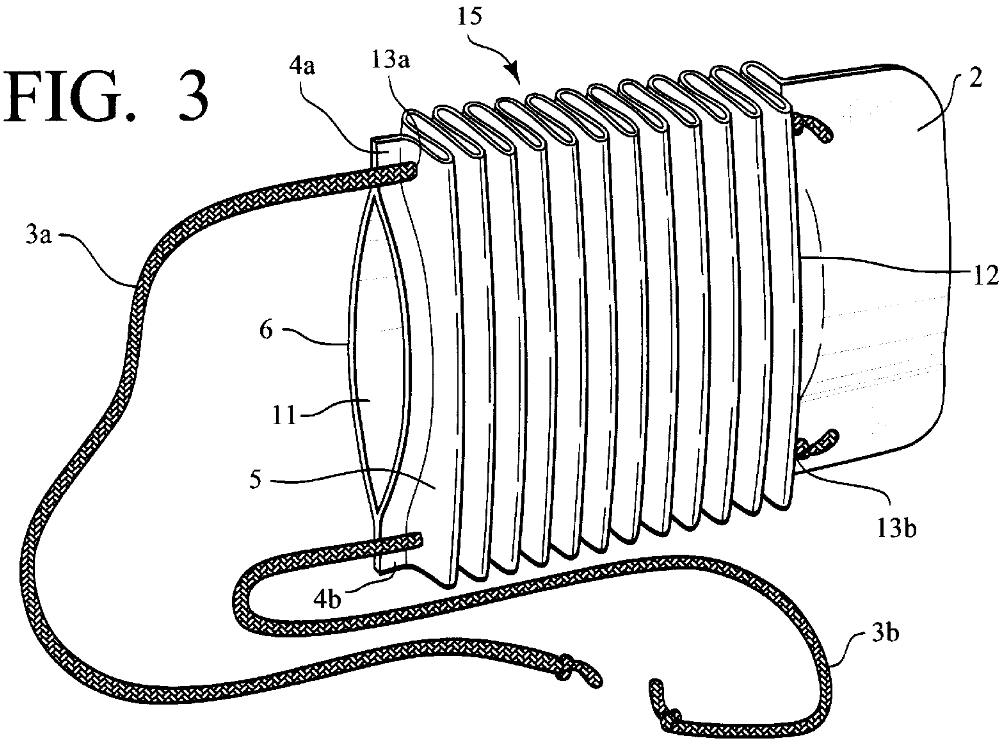
FIG. 3 is a perspective view of the gait belt cover of FIG. 1, showing the cover of the present invention in a shirred state with threads 3*a* and 3*b* pulled through one side of the cover.
Figure 4:
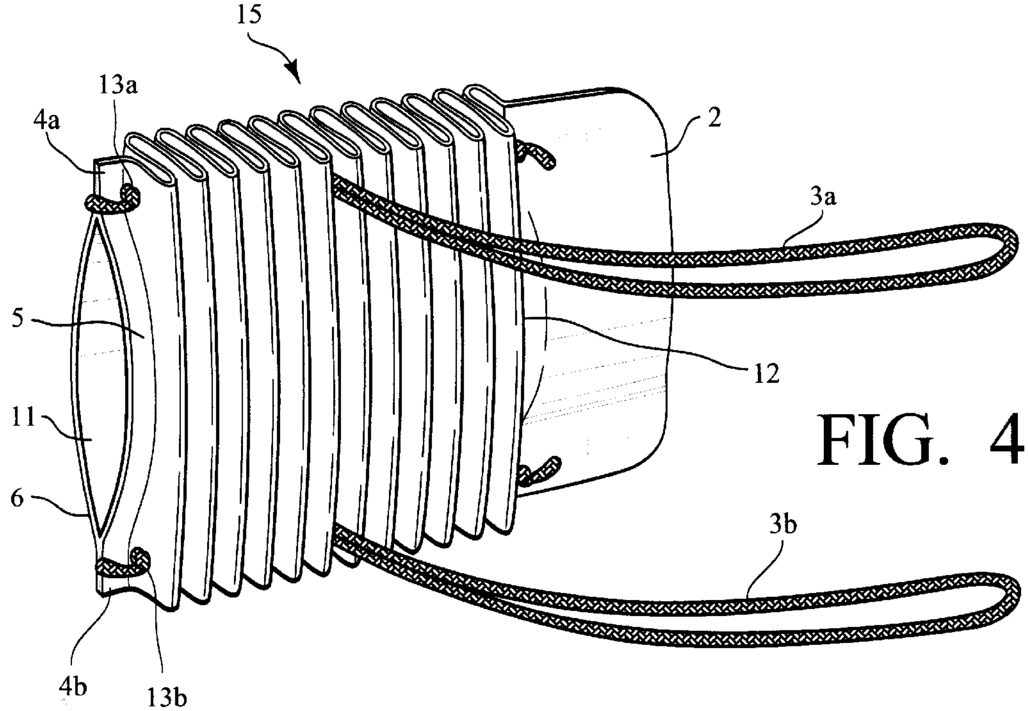
FIG. 4 is another perspective view of the gait belt cover of FIG. 1 showing the threads 3*a* and 3*b* secured at both ends of the cover and pulled from within the middle of the cover thereby shirring it.

As shown in FIG. 3 and FIG. 4, upon partial removal of top thread 3*a* and bottom thread 3*b* from top seam 4*a* and bottom seam 4*b*, respectively, belt cover 1 may be shirred into a bundle 15. The bundle 15 may be secured by tying the threads 3*a* and 3*b* around the bundle 15 or by tying knots into thread 3*a* and 3*b* at the edges of the bundle 15, as shown in FIG. 8 and FIG. 7, respectively. The bundled shirred belt cover 15 may be stored in this configuration until use or may be so configured just prior to use.

As shown in FIG. 5, a gait, or other type, belt 16 can be inserted into either opening 11 or 12 of shirred belt cover 1. Once the belt 16 is inserted, shirred belt cover I may be unshirred and extended along the length of the gait belt 16, as shown in FIG. 6. Flap 2 may be placed between buckle 17 and the wearer, not shown.

FIG. 9 shows another embodiment in which the cover 1 comprises only one panel 121 that is folded once and includes only one seam 123 that is formed from the joining of the opposing edges 124 and 125 of the panel. The cover 101 may be shirred and then maintained in a bundle by looping at least two threads, bands, clips or other similar restraining devices through the openings 111 and 112 and around the cover 101. The restraining devices 126 and 127 may then be secured by tying, knotting or other similar methods, thereby securing the bundle 115 until it is to be used, as shown in FIG. 10.

It will be realized that various changes may be made to the specific embodiment shown and described without departing from the scope and spirit of the present invention.

What is claimed is:

1. A device for supporting a person, comprising:

(a) a gait belt; and (b) a shirrable cover enveloping said gait belt, said shirrable cover being comprised of a sleeve and a flap, said flap extending outward from the end of said sleeve wherein said sleeve is formed from a front panel and a back panel, each of said front panel and said back panel having a top and bottom edge joined together forming an opening there between, said opening receiving said gait belt;

said back panel having a flap which extends longitudinally beyond said opening.

2. A device for supporting the lower back and abdominal region of a wearer, comprising:

(a) a belt; and (b) a shirrable cover enveloping said belt, said shirrable cover being comprised of a sleeve and a flap, within which said belt is disposed, whereby said shirable cover forms a complete barrier between said belt and said wearer and wherein said shirable cover is comprised of a front panel and a back panel, said front and back panel having a top and bottom edge respectfully, said top and bottom edge of said front panel and of said back panel being joined by a seam along said top edge and a seam along said bottom edge, said belt held between said seam along said top and bottom edge.

* * * * *